US010016273B2

(12) United States Patent
Keogh

(10) Patent No.: US 10,016,273 B2
(45) Date of Patent: Jul. 10, 2018

(54) FILTERED SEALING COMPONENTS FOR A TRANSCATHETER VALVE PROSTHESIS

(71) Applicant: Medtronic, Inc., Minneapolis, MN (US)

(72) Inventor: James R. Keogh, Maplewood, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 21 days.

(21) Appl. No.: 14/731,629

(22) Filed: Jun. 5, 2015

(65) Prior Publication Data

US 2016/0354201 A1  Dec. 8, 2016

(51) Int. Cl.
*A61F 2/24* (2006.01)

(52) U.S. Cl.
CPC .......... *A61F 2/2418* (2013.01); *A61F 2/2412* (2013.01); *A61F 2230/001* (2013.01); *A61F 2230/0065* (2013.01); *A61F 2250/0003* (2013.01); *A61F 2250/007* (2013.01); *A61F 2250/0039* (2013.01); *A61F 2250/0069* (2013.01)

(58) Field of Classification Search
None
See application file for complete search history.

(56) References Cited

U.S. PATENT DOCUMENTS

| 5,957,949 | A | 9/1999 | Leonhardt et al. |
|---|---|---|---|
| 6,015,431 | A | 1/2000 | Thornton et al. |
| 6,729,356 | B1 | 5/2004 | Baker et al. |
| 7,044,966 | B2 | 5/2006 | Svanidze et al. |
| 7,276,078 | B2 | 10/2007 | Spenser et al. |
| 7,331,991 | B2 | 2/2008 | Kheradvar et al. |
| 7,524,331 | B2 | 4/2009 | Birdsall |
| 7,534,261 | B2 | 5/2009 | Friedman |
| 7,628,805 | B2 | 12/2009 | Spenser et al. |
| 7,708,775 | B2 | 5/2010 | Rowe et al. |
| 7,780,725 | B2 | 8/2010 | Haug et al. |
| 7,972,378 | B2 | 7/2011 | Tabor et al. |
| 8,118,856 | B2 | 2/2012 | Schreck et al. |
| 8,142,497 | B2 | 3/2012 | Friedman |
| 8,182,528 | B2 | 5/2012 | Salahieh et al. |
| 8,231,670 | B2 | 7/2012 | Salahieh et al. |
| 8,449,599 | B2 | 5/2013 | Chau et al. |
| 8,603,160 | B2 | 12/2013 | Salahieh et al. |
| 8,623,078 | B2 | 1/2014 | Salahieh et al. |
| 8,628,566 | B2 | 1/2014 | Eberhardt et al. |
| 8,641,757 | B2 | 2/2014 | Pintor et al. |
| 8,668,733 | B2 | 3/2014 | Salahieh et al. |

(Continued)

FOREIGN PATENT DOCUMENTS

| WO | WO2014/072439 | 5/2014 | |
|---|---|---|---|
| WO | WO 2015055652 A1 * | 4/2015 | ............. A61L 27/18 |

*Primary Examiner* — Thomas J Sweet
*Assistant Examiner* — Megan Wolf
(74) *Attorney, Agent, or Firm* — Medler Ferro Woodhouse & Mills PLLC

(57) ABSTRACT

A transcatheter valve prosthesis includes a stent having a compressed configuration for delivery within a vasculature and an expanded configuration for deployment within a native heart valve and a prosthetic valve component disposed within and secured to the stent. A compartment is coupled to the stent, and a filtered opening into the compartment is configured to permit blood flow there-through and to trap emboli in the blood flow within the compartment.

10 Claims, 8 Drawing Sheets

(56) References Cited

U.S. PATENT DOCUMENTS

| | | |
|---|---|---|
| 8,673,000 B2 | 3/2014 | Tabor et al. |
| 8,734,484 B2 | 5/2014 | Ahlberg et al. |
| 8,795,357 B2 | 8/2014 | Yohanan et al. |
| 8,801,706 B2 | 8/2014 | Rothstein et al. |
| 8,801,776 B2 | 8/2014 | House et al. |
| 8,808,356 B2 | 8/2014 | Braido et al. |
| 8,852,272 B2 | 10/2014 | Gross et al. |
| 8,926,690 B2 | 1/2015 | Kovalsky |
| 8,986,371 B2 | 3/2015 | Quill et al. |
| 8,986,375 B2 | 3/2015 | Garde et al. |
| 8,992,608 B2 | 3/2015 | Haug et al. |
| 2003/0199963 A1 | 10/2003 | Tower et al. |
| 2003/0199971 A1 | 10/2003 | Tower et al. |
| 2004/0098096 A1 | 5/2004 | Eton |
| 2004/0111111 A1 | 6/2004 | Lin |
| 2007/0233175 A1* | 10/2007 | Zaver ............... A61F 2/013 606/200 |
| 2007/0244544 A1 | 10/2007 | Birdsall et al. |
| 2007/0270944 A1 | 11/2007 | Bergheim et al. |
| 2008/0275540 A1 | 11/2008 | Wen |
| 2009/0099653 A1 | 4/2009 | Suri et al. |
| 2009/0112311 A1 | 4/2009 | Miles et al. |
| 2009/0192591 A1 | 7/2009 | Ryan et al. |
| 2010/0036479 A1 | 2/2010 | Hill et al. |
| 2010/0168844 A1 | 7/2010 | Toomes et al. |
| 2010/0198238 A1 | 8/2010 | Sorajja |
| 2011/0172765 A1 | 7/2011 | Nguyen et al. |
| 2011/0257721 A1 | 10/2011 | Tabor |
| 2011/0264206 A1 | 10/2011 | Tabor |
| 2012/0035722 A1 | 2/2012 | Tuval |
| 2012/0041549 A1 | 2/2012 | Salahieh et al. |
| 2012/0101572 A1 | 4/2012 | Kovalsky et al. |
| 2012/0123529 A1 | 5/2012 | Levi et al. |
| 2013/0030519 A1 | 1/2013 | Tran et al. |
| 2013/0190857 A1 | 7/2013 | Mitra et al. |
| 2013/0190862 A1 | 7/2013 | Pintor et al. |
| 2013/0197622 A1 | 8/2013 | Mitra et al. |
| 2013/0245753 A1 | 9/2013 | Alkhatib |
| 2013/0274873 A1 | 10/2013 | Delaloye et al. |
| 2013/0331929 A1 | 12/2013 | Mitra et al. |
| 2013/0338765 A1 | 12/2013 | Braido et al. |
| 2014/0046426 A1 | 2/2014 | Kovalsky |
| 2014/0100650 A1 | 4/2014 | Chobotov |
| 2014/0107772 A1 | 4/2014 | Li et al. |
| 2014/0114402 A1 | 4/2014 | Ahlberg et al. |
| 2014/0114406 A1 | 4/2014 | Salahieh et al. |
| 2014/0194975 A1 | 7/2014 | Quill et al. |
| 2014/0194981 A1 | 7/2014 | Menk et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0243969 A1 | 8/2014 | Venkatasubramanian et al. |
| 2014/0257475 A1 | 9/2014 | Gross et al. |
| 2014/0277388 A1 | 9/2014 | Skemp |
| 2014/0277413 A1 | 9/2014 | Richter et al. |
| 2014/0277417 A1 | 9/2014 | Schraut et al. |
| 2014/0277419 A1 | 9/2014 | Garde et al. |
| 2014/0277422 A1 | 9/2014 | Ratz et al. |
| 2014/0277423 A1 | 9/2014 | Alkhatib et al. |
| 2014/0277424 A1 | 9/2014 | Oslund |
| 2014/0277425 A1 | 9/2014 | Dakin |
| 2014/0277426 A1 | 9/2014 | Dakin et al. |
| 2014/0277428 A1 | 9/2014 | Skemp et al. |
| 2014/0296975 A1 | 10/2014 | Tegels et al. |
| 2014/0316516 A1 | 10/2014 | Vidlund et al. |
| 2014/0350663 A1 | 11/2014 | Braido et al. |
| 2014/0350665 A1 | 11/2014 | Braido et al. |
| 2014/0350667 A1 | 11/2014 | Braido et al. |
| 2014/0350668 A1 | 11/2014 | Delaloye et al. |
| 2015/0005863 A1 | 1/2015 | Para |
| 2015/0073540 A1 | 3/2015 | Salahieh et al. |
| 2015/0073541 A1 | 3/2015 | Salahieh et al. |
| 2015/0073544 A1 | 3/2015 | Gorman, III et al. |
| 2015/0073548 A1 | 3/2015 | Matheny |
| 2015/0209136 A1* | 7/2015 | Braido ............... A61F 2/2403 623/2.18 |

* cited by examiner

FILTERED SEALING COMPONENTS FOR A TRANSCATHETER VALVE PROSTHESIS

FIELD OF THE INVENTION

The present invention relates to transcatheter valve prostheses and one or more filtered sealing components formed on a surface of a transcatheter valve prosthesis for preventing paravalvular leakage.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to filtered sealing components coupled to the valve prosthesis to prevent paravalvular leakage.

BRIEF SUMMARY OF THE INVENTION

Embodiments hereof relate to a transcatheter valve prosthesis that includes a stent having a compressed configuration for delivery within a vasculature and an expanded configuration for deployment within a native heart valve and a prosthetic valve component disposed within and secured to the stent. A compartment is coupled to the stent, and a filtered opening into the compartment is configured to permit blood flow there-through and to trap emboli in the blood flow within the compartment.

According to another embodiment hereof, a transcatheter valve prosthesis includes a stent having a compressed configuration for delivery within a vasculature and an expanded configuration for deployment within a native heart valve and a prosthetic valve component disposed within and secured to the stent. A skirt is coupled to an exterior of the stent. The skirt has a first edge coupled to the stent and an opposing second edge not coupled to the stent to form a pocket having an open end between the second edge of the skirt and the exterior of the stent. A filter is coupled to the skirt and the exterior of the stent. The filter extends over the open end of the pocket and is configured to permit blood flow there-through and to trap emboli in the blood flow within the pocket.

According to another embodiment hereof, a transcatheter valve prosthesis includes a stent having a compressed configuration for delivery within a vasculature and an expanded configuration for deployment within a native heart valve and a prosthetic valve component disposed within and secured to the stent. A compartment is coupled to the stent. The compartment is formed from a mesh. A coating is selectively applied to the mesh to form a solid portion and a filter portion. The solid portion does not allow blood flow there-through and the filter portion is configured to permit blood flow there-through and to trap emboli in the blood flow within the compartment.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
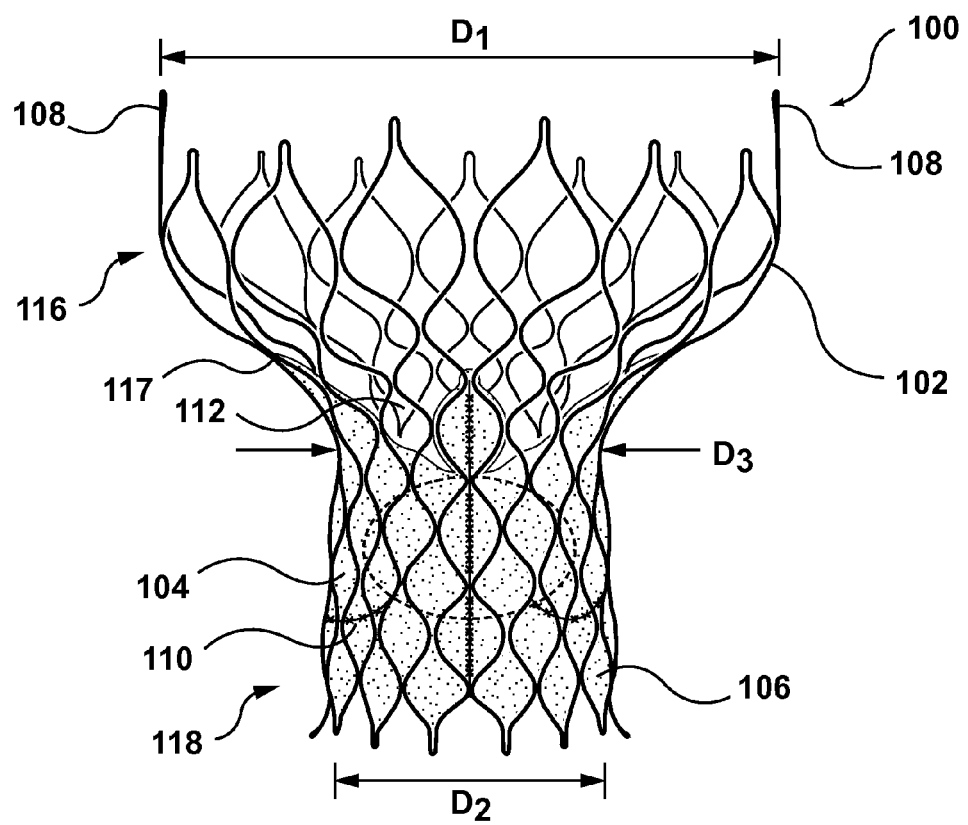
FIG. 1 is a side view illustration of an exemplary transcatheter heart valve prosthesis for use in embodiments hereof.

FIG. 1 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent 102 that supports a prosthetic valve component within the interior of stent 102. Stent 102 is a generally tubular support structure that defines a lumen there-through. Stent 102 is a frame or scaffold that defines a plurality of diamond or kite-shaped openings 112, with each diamond-shaped opening being defined by four vertexes or vertices and four segments or struts extending or formed between vertexes. In this embodiment, the frame has a lattice configuration which is laser cut from a tube and is formed as a unitary structure or component. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

Figure 1A:
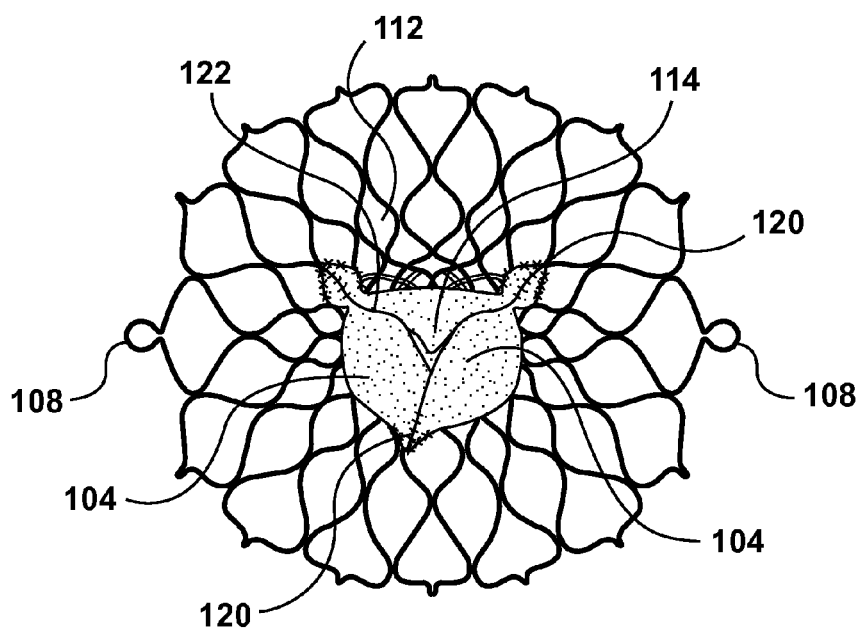
FIG. 1A is a top view illustration of the heart valve prosthesis of FIG. 1.
Figures 1B, 1C:
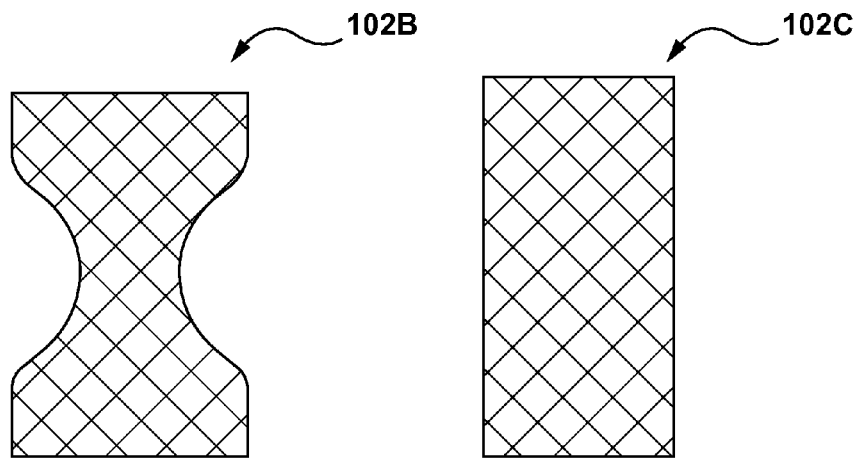
FIG. 1B is a side view illustration of an alternative configuration of a heart valve prosthesis for use in embodiments hereof.
FIG. 1C is a side view illustration of an alternative configuration of a heart valve prosthesis for use in embodiments hereof.

In the embodiment depicted in FIGS. 1 and 1A, stent 102 of valve prosthesis 100 has a deployed asymmetric hourglass configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed configuration of FIGS. 1 and 1A, the stent/valve support frame may have an hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if heart valve prosthesis 100 is configured for placement within a native valve having three leaflets such as the aortic, tricuspid, or pulmonary valves, heart valve prosthesis 100 includes three valve leaflets 104. If heart valve prosthesis 100 is configured for placement within a native valve having two leaflets such as the mitral valve, heart valve prosthesis 100 includes two valve leaflets 104. Valve leaflets 104 are sutured or otherwise securely and sealingly attached to the interior surface of stent 102 and/or graft material 106 which encloses or lines a portion of stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which is attached or coupled to an interior or exterior surface of the stent. In an embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In an embodiment shown in FIG. 1, graft material 106 extends from leaflets bases 110 to second end 118 of heart valve prosthesis.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve. Alternatively, heart valve prosthesis 100 may be balloon-expandable and delivery thereof may be accomplished via a balloon catheter as would be understood by one of ordinary skill in the art. Heart valve prosthesis 100 may be self-expandable, balloon-expandable, mechanically-expandable, or some combination thereof.

Figure 2:
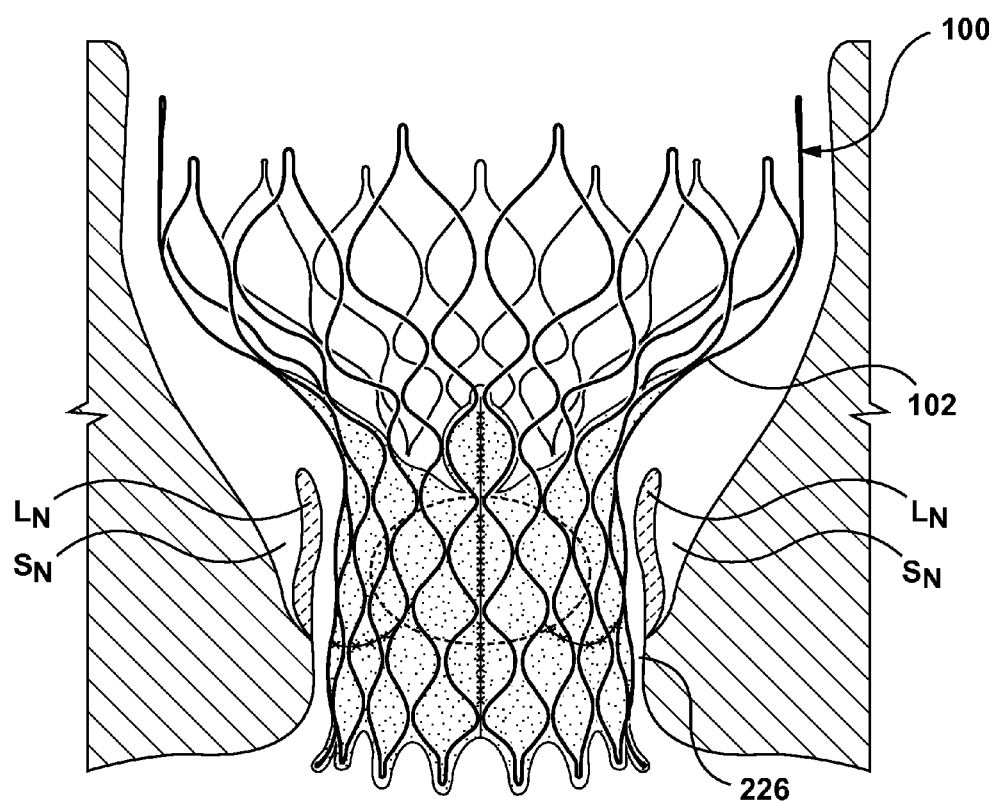
FIG. 2 is a side view illustration of the heart valve prosthesis of FIG. 1 implanted within a native valve annulus.

FIG. 2 is a side view illustration of heart valve prosthesis 100 implanted within a native aortic heart valve, which is shown in section, having native leaflets $L_N$ and corresponding native sinuses $S_N$. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or cavities/crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Embodiments hereof relate to a heart valve prosthesis having a filtered sealing component coupled thereto in order to occlude or fill gaps between the perimeter of a heart valve prosthesis and the native valve annulus, thereby reducing, minimizing, or eliminating leaks there through. The filtered sealing component forms or defines a compartment coupled to the heart valve prosthesis, and also includes a filtered opening into the compartment that is configured to permit blood flow there-through and to trap emboli in the blood flow within the compartment. Stated another way, blood is permitted to flow into the compartment via the filtered opening but any emboli or blood clots that may form or develop within the compartment are trapped within the compartment and therefore prevented from being released into a patient's bloodstream.

Figures 3, 4:
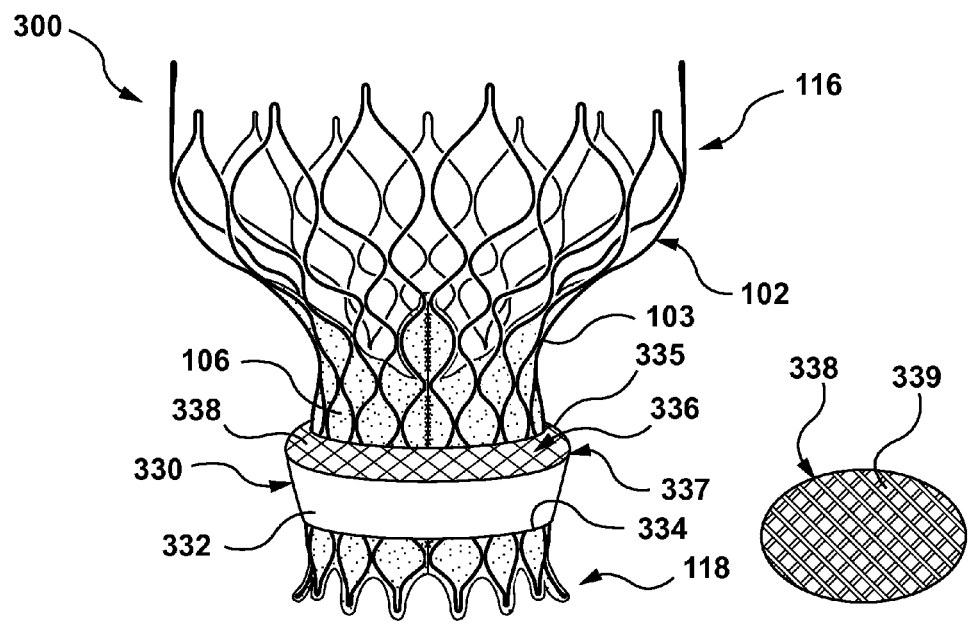
FIG. 3 is a side view illustration of a heart valve prosthesis including a filtered sealing component around an outer surface thereof, wherein the filtered sealing component includes a skirt that forms an open-ended pocket and a filter positioned over the open end of the pocket.
FIG. 4 is an enlarged view of a portion of the filter of FIG. 3.

In a first embodiment depicted in FIG. 3, a filtered sealing component 330 includes a skirt 332 formed of a flexible material that forms an annular open-ended compartment or pocket 336 and a filter 338 positioned over an open end 337 of the pocket. In this embodiment, open end 337 and filter 338 disposed there-over may be collectively considered a filtered opening into pocket 336. More particularly, skirt 332 is coupled to an exterior or outer surface 103 of stent 102. Skirt 332 is a flap of material having a first end or edge 334 attached to outer surface 103 of stent 102 and an opposing second end or edge 335 not coupled to stent 102 to form pocket 336 having open end 337 between second edge 335 of skirt 332 and outer surface 103 of stent 102. Stated another way, second edge 335 of skirt 332 is radially spaced apart from outer surface 103 of stent 102 and annular pocket 336 is formed between skirt 332 and stent 102, which includes graft material 106 that encloses or lines a portion of stent 102. First edge 334 of skirt 332 may be attached to stent 102 by any suitable means known to those skilled in the art, for example and not by way of limitation, welding, adhesive, suture, or mechanical coupling. Skirt 332 is formed from a material that does not allow blood flow there-through. Suitable materials for skirt 332 include but are not limited to a low-porosity woven fabric such as polyester, Dacron fabric, or PTFE. Porous materials advantageously provide a medium for tissue ingrowth. Further, skirt 332 may be pericardial tissue or may be a knit or woven polyester, such as a polyester or polytetrafluoroethylene (PTFE) knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side. Elastomeric materials such as but not limited to polyurethane may also be used as a material for skirt 332.

Filter 338 extends over open end 337 of pocket 336 and is coupled to second edge 335 of skirt 332 and outer surface 103 of stent 102. Filter 338 is configured to permit blood flow there-through and to trap emboli in the blood flow within the pocket. More particularly, in situ, blood flow between the perimeter of heart valve prosthesis 300 and the native valve annulus blood is permitted to flow through filter 338 into pocket 336 to thereby fill pocket 336 with blood. For example, retrograde blood flow may flow through filter 338 and enter pocket 336 when heart valve prosthesis 300 is configured for placement within an aorta valve. As pocket 336 fills with blood, skirt 332 (which forms the outer surface of pocket 336) radially or outwardly expands into and substantially fills any/all gaps or cavities/crevices between outer surface 103 of stent 102 and native valve tissue. Stated another way, once pocket 336 is filled with blood, filtered sealing component 330 functions as a continuous circumferential seal around heart valve prosthesis 300 to block or prevent blood flow around the outer perimeter of the prosthesis, thereby minimizing and/or eliminating any paravalvular leakage at the implantation site. However, once blood is positioned within the interior volume of pocket 336, emboli or blood clots may form within the interior volume of pocket 336 due to blood stagnation. Filter 338 is configured to trap or capture such emboli or blood clots within the interior volume of pocket 336 to thereby prevent such emboli or blood clots from being released into the patient's bloodstream.

In an embodiment hereof, as best shown in FIG. 4 which is an enlarged view of a portion of filter 338, filter 338 is formed from a mesh that defines openings or pores 339 sized or configured to provide protection from emboli or clots that may form within the blood contained within pocket 336. In an embodiment, filter 338 is formed from a plurality of metallic and/or polymeric wires or filaments woven together. In another embodiment, filter 338 may be constructed from a stamped metallic mesh material. Non-exhaustive examples of metallic materials for use in making filter 338 are stainless steel, cobalt based alloys such as 605L or MP35N, titanium, tantalum, and superelastic nickel-titanium alloy, such as Nitinol. In another embodiment, filter 338 is formed of a film material, such as nylon or PET film, that has holes poked there-through. In another embodiment, filter 338 may comprise woven or non-woven fabric or material. In another embodiment, filter 338 may comprise polyethylene fibers or yarn. The size of pores 339 can vary from 50 to 300 microns. The pore size can be selected based on the optimization of blood flow or embolization protection. For example, relatively large pore sizes allow higher blood flow rates while relatively small pore sizes trap smaller emboli. In an embodiment, the pore size may be roughly 100 microns.

Notably, once blood is positioned within or fills the interior volume of pocket 336, any emboli or blood clots that form within the interior volume of pocket 336 may then function to retain or hold blood in the pocket. More particularly, since filter 338 is configured to trap such emboli or blood clots in the pocket, the emboli or blood clots may block or cover pores 339 defined by filter 338. When pores 339 of filter 338 are blocked, any blood contained within pocket 336 is essentially trapped or held within the pocket in order to form a permanent seal. As explained above, the blood-filled pocket 336 substantially fills any/all gaps or cavities/crevices between outer surface 103 of stent 102 and native valve tissue so that filtered sealing component 330 functions as a continuous circumferential seal around heart valve prosthesis 300.

Although embodiments depicted herein illustrate open-ended pocket 336 of filtered sealing component 330 oriented to catch retrograde blood flow, it would be obvious to one of ordinary skill in the art that pocket 336 may be inverted to catch antegrade flow rather than retrograde flow. More particularly, in the embodiment of FIG. 3, first end or edge 334 of skirt 332 is attached or coupled to outer surface 103 of stent 102 adjacent to second end 118 thereof. Skirt 332 extends in a direction towards first end 116 of stent 102. However, in another embodiment hereof (not shown), open-ended annular pocket 336 can be oriented in the opposite direction (i.e., to prevent forward blood flow), with its open side facing generally towards second end 118 of heart valve prosthesis rather than facing generally towards first end 116 of heart valve prosthesis.

In the embodiment of FIG. 3, filtered sealing component 330 is coupled to outer surface 103 of heart valve prosthesis 300 along or adjacent to constriction region 117 thereof, described with respect to FIG. 1 above. When deployed, filtered sealing component 330 may be positioned in situ at the native valve annulus, slightly above the valve annulus, slightly below the valve annulus, or some combination thereof. Since the annular filtered sealing component is coupled to outer surface 103 of heart valve prosthesis 300, longitudinal placement and/or the size and shape thereof is flexible and may be adjusted or adapted according to each application and to a patient's unique needs. For example, depending on the anatomy of the particular patient, the filtered sealing component may be positioned on heart valve prosthesis 300 so that in situ the filtered sealing component is positioned between heart valve prosthesis 300 and the interior surfaces of the native valve leaflets, between heart valve prosthesis 300 and the interior surfaces of the native valve annulus, and/or between heart valve prosthesis 300 and the interior surfaces of the left ventricular outflow track (LVOT).

In another embodiment hereof, filtered sealing component 330 may include an expandable control ring (not shown) coupled to the second or unattached edge of skirt 332 which operates to radially extend or deploy unattached second edge 335 of skirt 332 outwardly away from stent 102 as described in U.S. Patent Application Publication No. 2014/0194981 to Menk et al., application Ser. No. 13/738,376, which is herein incorporated by reference in its entirety. The expandable control ring may be formed from a self-expanding material or may have an adjustable diameter that may be varied in situ to selectively extend the unattached second edge 335 of skirt 332 outwardly away from the outer surface of the heart valve prosthesis.

Figure 5:
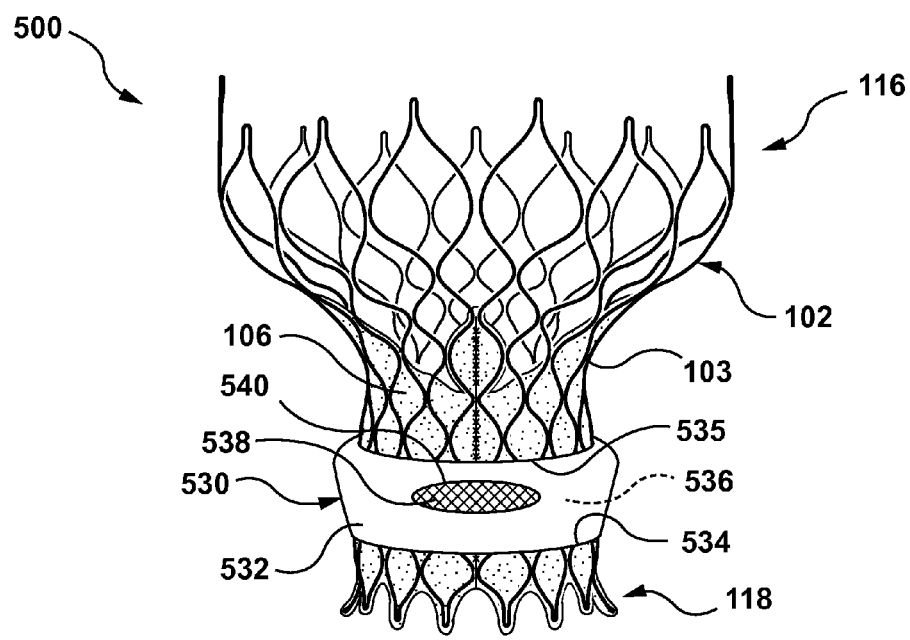
FIG. 5 is a side view illustration of a heart valve prosthesis including a filtered sealing component around an outer surface thereof according to another embodiment hereof, wherein the filtered sealing component includes a skirt that forms a compartment and a filter positioned over an opening formed on the skirt.

In the embodiment of FIG. 3, filter 338 is annular and extends over open end 337 of pocket 336. However, the filter may have different configurations and placements. For example, FIG. 5 illustrates a heart valve prosthesis 500 having a filtered sealing component 530 according to another embodiment hereof. The filtered sealing component includes a skirt 532 formed of a flexible material that forms an annular compartment 536 and a filter 538 positioned over an opening or inlet 540 formed on skirt 532. Opening 540 and filter 538 disposed there-over may be collectively considered a filtered opening into compartment 536. More particularly, skirt 532 is similar to skirt 332 except that skirt 532 has a first end or edge 534 and an opposing second end or edge 535 that are both attached to outer surface 103 of stent 102. With both edges 534, 535 attached to stent 102, skirt 532 forms annular compartment 536 between skirt 532 and stent 102. Stated another way, except for opening 540, compartment 536 may be considered enclosed or sealed since both first and second opposing edges 534, 535 of skirt 532 are coupled to stent 102, which includes graft material 106 that encloses or lines a portion of stent 102. First and second opposing edges 534, 535 of skirt 532 may be attached to stent 102 by any suitable means known to those skilled in the art, for example and not by way of limitation, welding, adhesive, suture, or mechanical coupling, and skirt 532 may be formed from similar materials as described above with respect to skirt 332.

In this embodiment, opening 540 is formed through skirt 532 that permits blood flow into the interior volume of compartment 536. In the embodiment of FIG. 5, opening 540 is oval-shaped but it will be understood by one of ordinary skill in the art that opening 540 may have any shape or configuration. Filter 538 extends over opening 540 and is coupled to skirt 532. Similar to filter 338, filter 538 is configured to permit blood flow there-through and to trap emboli in the blood flow within compartment 536. Once blood is positioned within the interior volume of compartment 536, the blood-filled compartment 536 substantially fills any/all gaps or cavities/crevices between outer surface 103 of stent 102 and native valve tissue and filtered sealing component 530 therefore functions as a continuous circumferential seal around heart valve prosthesis 500 to block or prevent blood flow around the outer perimeter of the prosthesis, thereby minimizing and/or eliminating any paravalvular leakage at the implantation site. However, once blood is positioned within the interior volume of compartment 536, emboli or blood clots may form within the interior volume of compartment 536 due to blood stagnation. Filter 538 is configured to trap or capture such emboli or blood clots within the interior volume of compartment 536 to thereby prevent such emboli or blood clots from being released into the patient's bloodstream. Similar to filter 338, filter 538 is formed from a mesh that defines openings or pores sized or configured to provide protection from emboli or clots that may form within the blood contained within compartment 536. Although filtered sealing component 530 is shown in FIG. 5 with only one filtered opening, filtered sealing component 530 may include a plurality of spaced-apart openings 540 that each include a filter 538 extending there-over.

Figure 6:
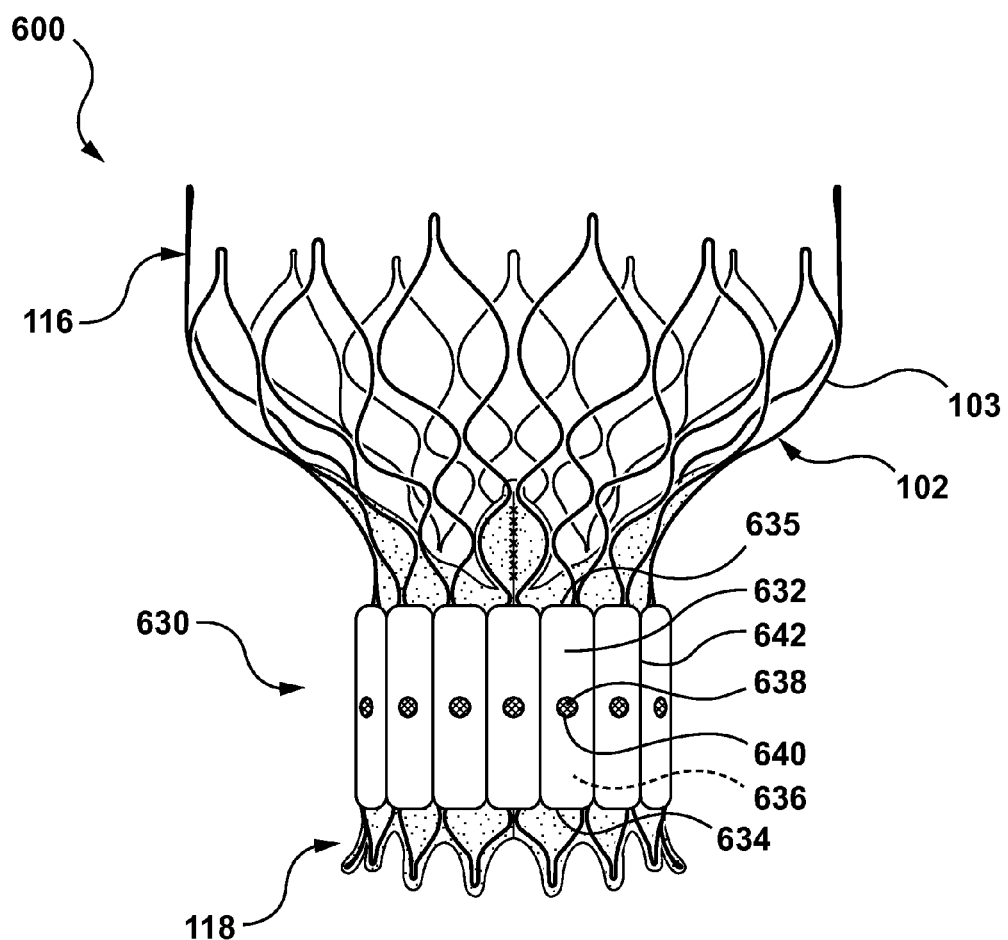
FIG. 6 is a side view illustration of a heart valve prosthesis including a filtered sealing component around an outer surface thereof according to another embodiment hereof, wherein the filtered sealing component includes a plurality of compartments and the filtered sealing component extends around the entire perimeter of the heart valve prosthesis.

In the embodiments of FIG. 3 and FIG. 5, the compartment or pocket formed by the filtered sealing component is annular. However, the filtered sealing component may include a plurality of compartments positioned around the exterior of the heart valve prosthesis. For example, FIG. 6 illustrates a heart valve prosthesis 600 having a filtered sealing component 630 according to another embodiment hereof. The filtered sealing component includes a skirt 632 formed of a flexible material that has first and second opposing edges 634, 635 coupled to stent 102 to form a plurality of pockets or compartments 636 between skirt 632 and outer surface 103 of stent 102, which includes graft material 106 that encloses or lines a portion of stent 102. Edges 634, 635 of skirt 632 may be attached to stent 102 by any suitable means known to those skilled in the art, for example and not by way of limitation, welding, adhesive, suture, or mechanical coupling. Skirt 632 may be formed from similar materials as described above with respect to skirt 332. As shown in FIG. 6, a plurality of dividers or seams 642 may be provided on skirt 632 to form the plurality of compartments 636 positioned around stent 102. The compartments can be formed in any number, size, and/or shape around stent 102. Although filtered sealing component 630 is shown in FIG. 6 as being positioned to extend around the full perimeter or outer surface 103 of stent 102, filtered sealing component 630 may include a plurality of spaced-apart compartments that each include a filtered opening formed therein. Further, although filtered sealing component 630 is described as being formed with a skirt 632 having seams 642, it will be understood by one of ordinary skill in the art that the plurality of compartments may be formed via a plurality of distinct or individual skirts rather than a single integral skirt having seams or dividers to form the plurality of compartments.

In this embodiment, each compartment 636 includes an opening or inlet 640 that is formed through skirt 632 that permits blood flow into the interior volume of the respective compartment 636. In the embodiment of FIG. 6, opening 640 are circular but it will be understood by one of ordinary skill in the art that openings 640 may have any shape or configuration. A filter 638 is positioned or extends over each opening or inlet 640. Openings 640 and filters 638 disposed there-over may be collectively considered a plurality of filtered openings into compartments 636. Filters 638 are coupled to skirt 632, and similar to filter 338, each filter 638 is configured to permit blood flow there-through and to trap emboli in the blood flow within its respective compartment 636. Once blood is positioned within the interior volume of compartments 636, the blood-filled compartments 636 substantially fill any/all gaps or cavities/crevices between outer surface 103 of stent 102 and native valve tissue and filtered sealing component 630 therefore functions as a circumferential seal around heart valve prosthesis 600 to block or prevent blood flow around the outer perimeter of the prosthesis, thereby minimizing and/or eliminating any paravalvular leakage at the implantation site. However, once blood is positioned within the interior volume of compartments 636, emboli or blood clots may form within the interior volume of compartments 636 due to blood stagnation. Filters 638 are configured to trap or capture such emboli or blood clots within the interior volume of compartments 636 to thereby prevent such emboli or blood clots from being released into the patient's bloodstream. Similar to filter 338, filters 638 are formed from a mesh that defines openings or pores sized or configured to provide protection from emboli or clots that may form within the blood contained within compartments 636.

Figure 6A:
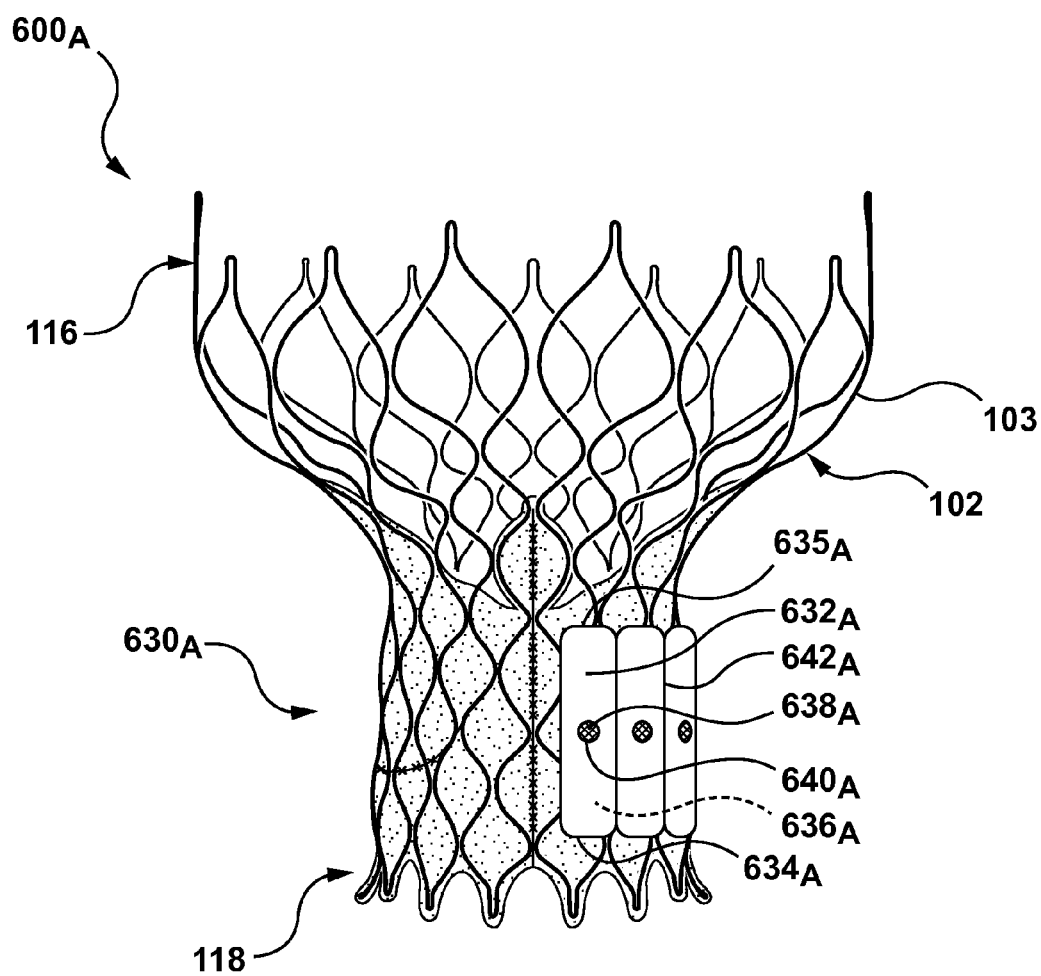
FIG. 6A is a side view illustration of a heart valve prosthesis including a filtered sealing component attached thereto according to another embodiment hereof, wherein the filtered sealing component includes a plurality of compartments and the filtered sealing component extends around a portion of the perimeter of the heart valve prosthesis.

As stated above, a filtered sealing component is not required to extend around the entire perimeter of a heart valve prosthesis. For example, in another embodiment hereof depicted in FIG. 6A, a heart valve prosthesis 600$_A$ has a filtered sealing component 630$_A$ that extends around only a portion of the perimeter of the heart valve prosthesis. Similar to filtered sealing component 630, filtered sealing component 630$_A$ includes a skirt 632$_A$ formed of a flexible material that has first and second opposing edges 634$_A$, 635$_A$ coupled to stent 102 to form a plurality of pockets or compartments 636$_A$ between skirt 632$_A$ and outer surface 103 of stent 102, which includes graft material 106 that encloses or lines a portion of stent 102. As shown in FIG. 6A, a plurality of dividers or seams 642$_A$ may be provided on skirt 632$_A$ to form the plurality of compartments 636$_A$ positioned around stent 102. In this embodiment, however, the plurality of compartments 636$_A$ are positioned around a portion of the perimeter of stent 102 and do not extend around the entire perimeter of the stent. Each compartment 636$_A$ includes an opening or inlet 640$_A$ that is formed through skirt 632$_A$ that permits blood flow into the interior volume of the respective compartment 636$_A$. A filter 638$_A$ is positioned or extends over each opening or inlet 640$_A$. Similar to filter 338, filters 638$_A$ are formed from a mesh that defines openings or pores sized or configured to provide protection from emboli or clots that may form within the blood contained within compartments 636$_A$. Openings 640$_A$ and filters 638$_A$ disposed there-over may be collectively considered a plurality of filtered openings into compartments 636$_A$.

Figure 11:
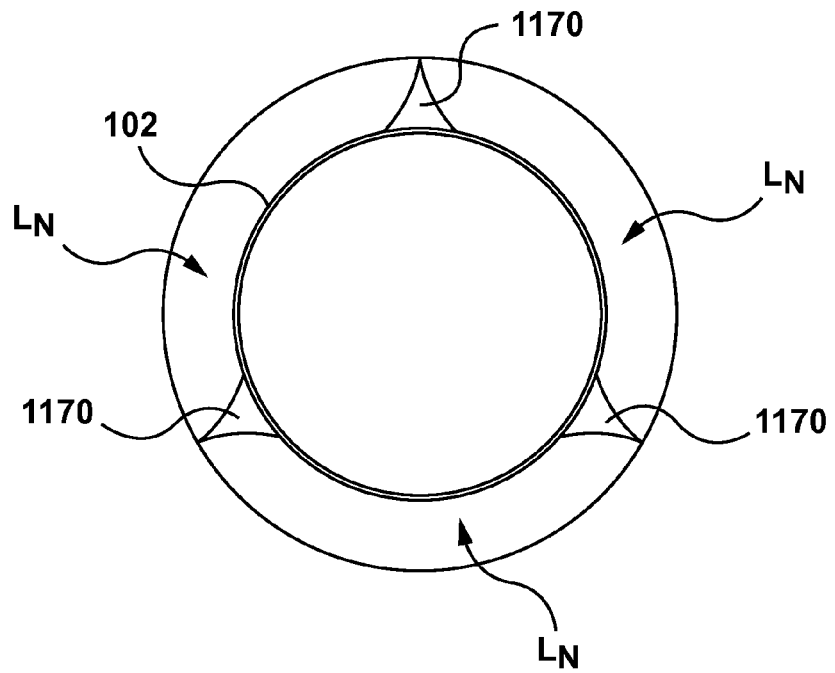
FIG. 11 is an end view illustration of the heart valve prosthesis of FIG. 1 implanted within a native valve annulus.
Figure 12:
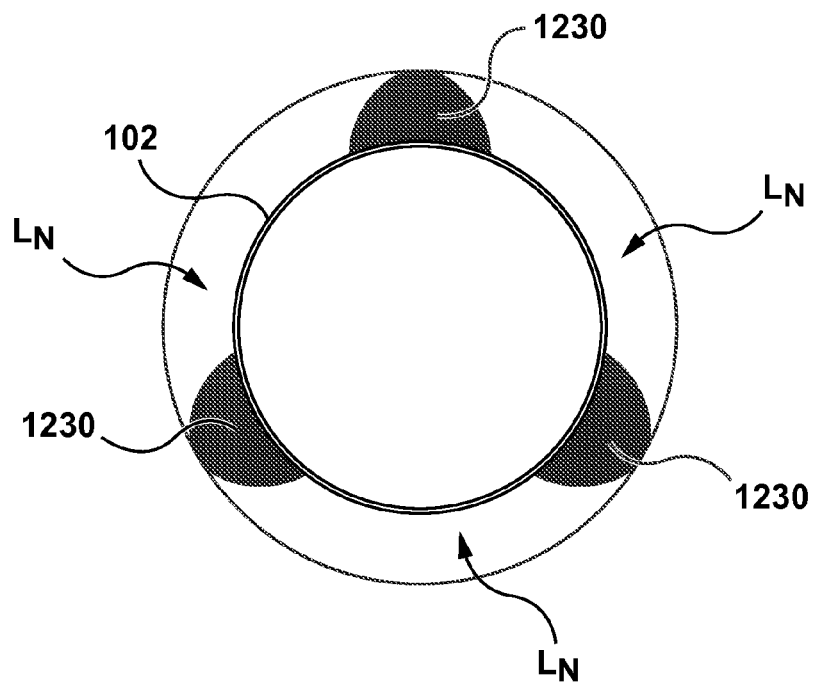
FIG. 12 is an end view illustration of a heart valve prosthesis including a plurality of filtered sealing components attached thereto implanted within a native valve annulus, wherein the sealing components are positioned within gaps formed at commissural points of the native valve leaflets.

In another embodiment hereof, depicted in FIGS. 11-12, a plurality of spaced-apart filtered sealing components may be positioned on the heart valve prosthesis. FIG. 11 is an end view illustration of stent 102 of heart valve prosthesis 100 implanted within a native aortic valve annulus, while FIG. 12 is an end view illustration of a heart valve prosthesis including a plurality of filtered sealing components 1230 attached thereto implanted within a native aortic valve annulus. As shown in FIGS. 11-12, native valve leaflets $L_N$ have been left in situ with stent 102 being implanted so as to be positioned radially within the native valve leaflets $L_N$. As best shown on FIG. 11, a plurality of gaps 1170 may be formed at commissural points of native valve leaflets $L_N$. As shown on FIG. 12, filtered sealing components 1230 are attached to an outer surface of stent 102 and configured to be disposed within gaps 1170 formed at the commissural points of native valve leaflets $L_N$. In an embodiment, each filtered sealing component 1230 may have a configuration similar to a single compartment 636 described above and include a skirt having an opening or inlet formed therein, the opening including a filter disposed thereover to provide protection from emboli or clots that may form within the blood contained within the compartment.

Figure 7:
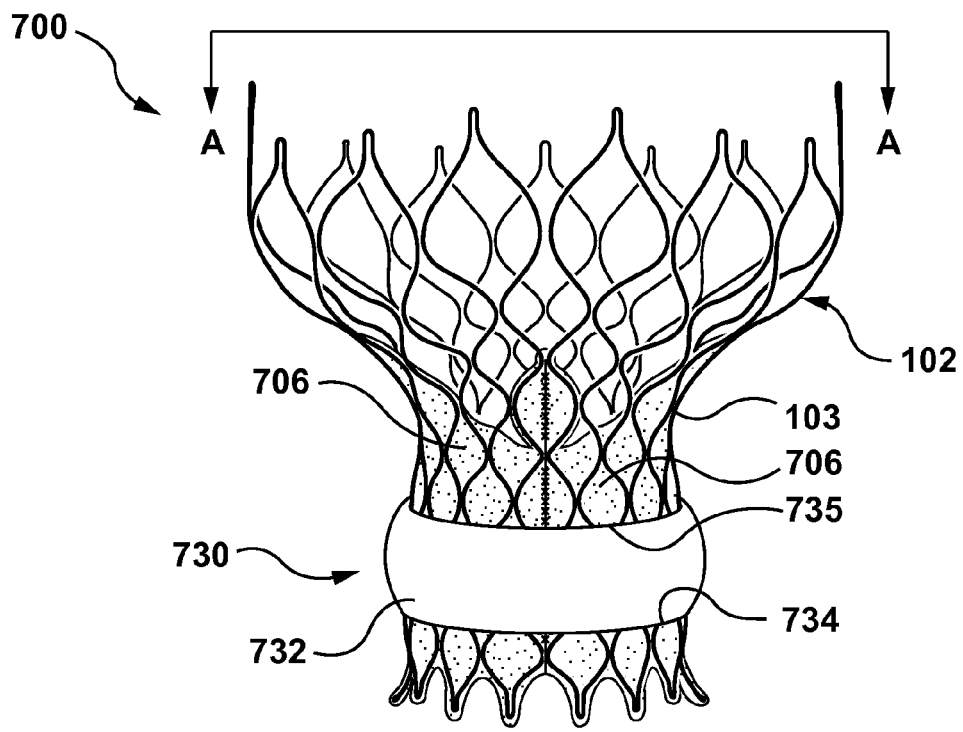
FIG. 7 is a side view illustration of a heart valve prosthesis including a filtered sealing component around an outer surface thereof according to another embodiment hereof, wherein the filtered sealing component includes a skirt that forms a compartment and a filter positioned over an opening formed through graft material of the heart valve prosthesis.
Figure 8:
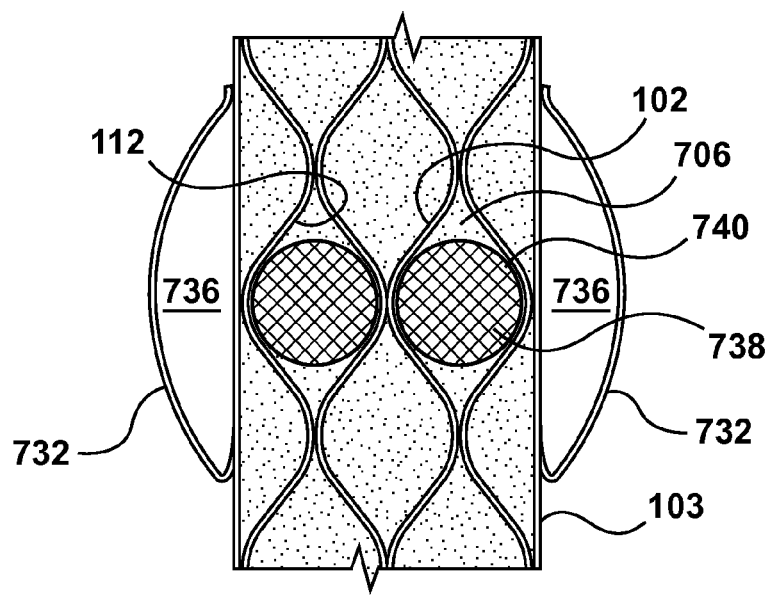
FIG. 8 is a cross-sectional view of a portion of FIG. 7 taken along line A-A of FIG. 7.

In the embodiments of FIGS. 3, 5, 6, 6A, and 12, the filtered opening of each filtered sealing component is formed on the exterior or outer surface of the heart valve prosthesis. However, the filtered opening may be formed on an interior or inner surface of the heart valve prosthesis. For example, FIGS. 7 and 8 illustrate a heart valve prosthesis 700 having a filtered sealing component 730 according to another embodiment hereof. The filtered sealing component includes a skirt 732 formed of a flexible material that forms an annular pocket or compartment 736 around the exterior of stent 102. One or more openings or inlets 740 are formed through graft material 706 which encloses or lines a portion of stent 102 and a filter 738 is positioned over each opening 740. Openings 740 and filters 738 disposed there-over may be collectively considered a plurality of filtered openings into compartment 736. More particularly, skirt 732 is similar to skirt 532 and has a first end or edge 734 and an opposing second end or edge 735 that are both attached to outer surface 103 of stent 102. With both edges 734, 735 attached to stent 102, skirt 732 forms annular pocket or compartment 736 between skirt 732 and stent 102. First and second opposing edges 734, 735 of skirt 732 may be attached to stent 102 by any suitable means known to those skilled in the art, for example and not by way of limitation, welding, adhesive, suture, or mechanical coupling, and skirt 732 may be formed from similar materials as described above with respect to skirt 332.

In this embodiment, as best shown on FIG. 7, openings or inlets 740 are formed through graft material 706 which encloses or lines a portion of stent 102. More particularly, openings 740 are formed through graft material 706 that is disposed or positioned over a diamond or kite-shaped opening 112 of stent 102 such that the interior of compartment 736 is in fluid communication with the lumen of stent 102. Openings 740 permit blood flow from the lumen of stent 102 into the interior volume of compartment 736. In the embodiment of FIG. 6, openings or inlets 740 are circular but it will be understood by one of ordinary skill in the art that openings 740 may have any shape or configuration. Filters 738 extend over each opening 740 and are coupled to graft material 706 and/or stent 102. Similar to filter 338, each filter 738 is configured to permit blood flow there-through and to trap emboli in the blood flow within compartment 736. Once blood is positioned within the interior volume of compartment 736, the blood-filled compartment 736 substantially fills any/all gaps or cavities/crevices between outer surface 103 of stent 102 and native valve tissue and filtered sealing component 730 therefore functions as a continuous circumferential seal around heart valve prosthesis 700 to block or prevent blood flow around the outer perimeter of the prosthesis, thereby minimizing and/or eliminating any paravalvular leakage at the implantation site. However, once blood is positioned within the interior volume of compartment 736, emboli or blood clots may form within the interior volume of compartment 736 due to blood stagnation. Filters 738 are configured to trap or capture such emboli or blood clots within the interior volume of compartment 736 to thereby prevent such emboli or blood clots from being released into the patient's bloodstream. Similar to filter 338, filters 738 are formed from a mesh that defines openings or pores sized or configured to provide protection from emboli or clots that may form within the blood contained within compartment 736.

In the embodiments described above with respect to FIGS. 3, 5, 6, 6A, and 12, each filtered sealing component 330, 530, 630, 630$_A$, 1230 is formed via a skirt of flexible material and a filter that extends of an opening formed in or by the skirt. Thus, in these embodiments, each filtered sealing component 330, 530, 630, 630$_A$, 1230 is formed or made from multiple or different materials including a solid skirt material and a mesh filter material that extends over an opening formed in or by the skirt. The different materials of the skirt and the filter may be coupled together via any mechanical means known in the art including be not limited to stitches, glue or adhesive, melting, staples, or the like. However, in another embodiment hereof, any of the above described filtered sealing components may be formed by a mesh material that is partially or selectively coated, i.e., dip coated, spray coated, or the like, to create portions that can act as a filter allowing fluid to pass through and other portions that act as a solid material that do not allow fluid to pass though. Stated another way, the compartment or pocket may be formed via a mesh and a coating is selectively applied to the mesh to form a solid portion, i.e., a skirt, and a filter portion, i.e., a filtered opening.

Figure 9:
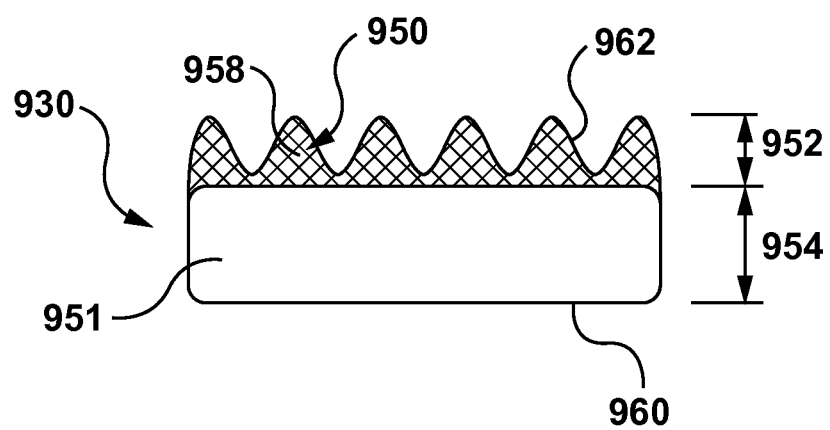
FIG. 9 is a side view illustration of a filtered sealing component removed from a heart valve prosthesis and laid out flat for illustrative purposes only, wherein the filtered sealing component is a mesh and includes a coating selectively applied thereto.

More particularly, FIG. 9 is a side view illustration of a filtered sealing component 930 removed from a heart valve prosthesis and laid out flat for illustrative purposes only. Filtered sealing component includes a mesh 950. When assembled onto a heart valve prosthesis, a first end or edge 960 and an opposing second end or edge 962 of mesh 950 are both attached to the outer surface of a stent to form an annular pocket or compartment. Similar to the mesh of filter 338 described above, mesh 950 defines openings or pores 958 sized or configured to provide protection from emboli or clots that may form within the blood contained within the annular pocket or compartment. In an embodiment, mesh 950 is formed from a plurality of metallic and/or polymeric wires or filaments woven together. In another embodiment, mesh 950 may be constructed from a stamped metallic mesh material. Suitable materials and pore sizes for mesh 950 are similar to those listed above with respect to filter 338.

A coating 951 is partially and selectively applied to mesh 950 in order to form a solid portion 954 and a filter portion 952. More particularly, coating 951 is applied to a portion of mesh 950 to form solid portion 954. With coating 951 applied thereto, solid portion 954 functions similar to skirts 332, 532, 632, 632$_A$ described above and does not allow blood flow there-through. Coating 951 is not applied to the remaining portion of mesh 950 to form filter portion 952. Without coating 951 applied thereto, filter portion 952 functions similar to the filtered openings described above (i.e., open end 337, opening 540, and opening 640/640$_A$ having filters 338, 538, 638/638$_A$, respectively, disposed there-over) and is configured to permit blood flow there-through but to trap emboli in the blood flow within the annular pocket or compartment. Stated another way, without coating 951 applied thereto, filter portion 952 includes only mesh 950 which functions the same as filters described above. Suitable materials for coating 951 include but are not limited to a resorbable material, a biodegradable material, a biomaterial, a polymeric material, a plastic material, collagen, and fibrin.

Figure 10:
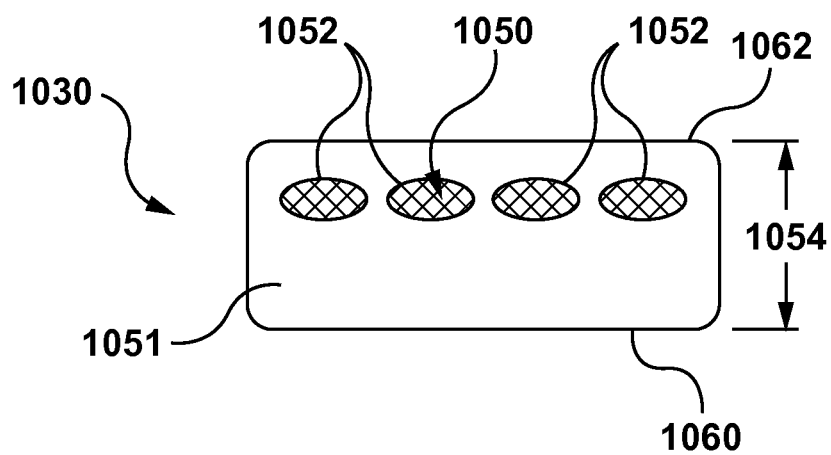
FIG. 10 is a side view illustration of a filtered sealing component according to another embodiment hereof, the filtered sealing component removed from a heart valve prosthesis and laid out flat for illustrative purposes only, wherein the filtered sealing component is a mesh and includes a coating selectively applied thereto.

In FIG. 9, filter portion 952 is annular and extends around the outer surface or perimeter of the stent when assembled onto the heart valve prosthesis, similar to filter 338 that is annular and extends over open end 337 of pocket 336 as described above with respect to FIG. 3. However, filter portion 952 may be formed with different configurations and patterns. For example, FIG. 10 illustrates an embodiment having a plurality of spaced-apart filter portions 1052. FIG. 10 is a side view illustration of a filtered sealing component 1030 removed from a heart valve prosthesis and laid out flat for illustrative purposes only. Filtered sealing component includes a mesh 1050 which is similar to mesh 950 described above. When assembled onto a heart valve prosthesis, a first end or edge 1060 and an opposing second end or edge 1062 of mesh 1050 are both attached to the outer surface of a stent to form an annular pocket or compartment. A coating 1051 is partially and selectively applied to mesh 1050 in order to form a solid portion 1054 and a plurality of spaced-apart filter portions 1052. For example, spaced-apart filter portions 1052 may be masked or covered during application of coating 1051 via a dip coating process, spray coating process, or the like. With coating 1051 applied thereto, solid portion 1054 does not allow blood flow there-through while filter portions 1052 which do not have any coating applied thereto are configured to permit blood flow there-through and to trap emboli in the blood flow within the annular pocket or compartment.

Although embodiments depicted herein illustrate one or more filtered sealing components integrated onto a heart valve prosthesis configured for implantation within an aortic valve, it would be obvious to one of ordinary skill in the art that the filtered sealing components as described herein may be integrated onto a heart valve prosthesis configured for implantation implanted within other heart valves, such as a mitral valve, tricuspid valve, or a pulmonary valve.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
   a stent having a compressed configuration for delivery within a vasculature and an expanded configuration for deployment within a native heart valve;
   a prosthetic valve component disposed within and secured to the stent;
   a graft material coupled to an outer surface or an inner surface of the stent;
   a skirt coupled to the outer surface of the stent, wherein the skirt is formed from a first portion of a single piece of mesh having a first plurality of openings and a coating is applied to the first portion of the single piece of mesh whereby blood flow is not allowed through the first plurality of openings of the first portion of the single piece of mesh and wherein the skirt includes first and second opposing edges that are attached to the stent at longitudinally spaced-apart locations such that an enclosed compartment is formed by the skirt and the graft material; and a filtered opening into the enclosed compartment configured to permit blood flow there-through and to trap emboli in the blood flow within the enclosed compartment, wherein the filtered opening is formed from a second portion of the single piece of mesh having a second plurality of openings and the coating is not applied to the second portion of the single piece of mesh so as to allow blood flow through the second plurality of openings of the second portion of the single piece of mesh, wherein the filtered opening is one of a plurality of spaced-apart filtered openings formed by a plurality of spaced-apart portions of the single piece of mesh that are uncoated by the coating.

2. The transcatheter valve prosthesis of claim 1, wherein the skirt encircles the outer surface of the stent and the enclosed compartment is annular.

3. The transcatheter valve prosthesis of claim 1, wherein the single piece of mesh has a pore size between 50 and 300 microns.

4. The transcatheter valve prosthesis of claim 1, wherein the skirt is one of a plurality of circumferentially spaced-apart skirts coupled to the stent and each skirt is positioned at a circumferentially spaced-apart location on the stent that corresponds to a commissural point of a native valve.

5. The transcatheter valve prosthesis of claim 1, wherein the filtered opening has a predetermined shape.

6. The transcatheter valve prosthesis of claim 5, wherein the predetermined shape is oval.

7. The transcatheter valve prosthesis of claim 1, wherein each filtered opening has a predetermined shape.

8. The transcatheter valve prosthesis of claim 7, wherein the predetermined shape is oval.

9. A transcatheter valve prosthesis comprising:
a stent having a compressed configuration for delivery within a vasculature and an expanded configuration for deployment within a native heart valve;
a prosthetic valve component disposed within and secured to the stent;
a graft material coupled to an outer surface or an inner surface of the stent;
a single piece of mesh coupled to the stent, wherein a compartment is formed by the single piece of mesh and the graft material; and
a coating selectively applied to the single piece of mesh to form a solid portion and a filter portion, the solid portion including a first plurality of openings of the single piece of mesh that are blocked by the coating and the filter portion including a second plurality of openings of the single piece of mesh that are uncoated by the coating, wherein the solid portion does not allow blood flow through the first plurality of openings of the single piece of mesh and the filter portion is configured to permit blood flow through the second plurality of openings of the single piece of mesh and to trap emboli in the blood flow within the compartment, wherein the filter portion is one of a plurality of spaced-apart filter portions formed by a plurality of spaced-apart portions of the single piece of mesh that are uncoated by the coating.

10. The transcatheter valve prosthesis of claim 9, wherein the compartment is coupled to the outer surface of the stent and is annular.

* * * * *